(12) United States Patent
Bou Chedid et al.

(10) Patent No.: US 8,981,093 B2
(45) Date of Patent: *Mar. 17, 2015

(54) PROCESS FOR PREPARING PIPERAZINE

(71) Applicant: BASF SE, Ludwigshafen (DE)

(72) Inventors: Roland Bou Chedid, Mannheim (DE); Johann-Peter Melder, Böhl-Iggelheim (DE); Ulrich Abel, Schifferstadt (DE); Roman Dostalek, Neuleiningen (DE); Nina Challand, Mannheim (DE); Bernd Stein, Alsbach-Hähnlein (DE); Michael Jödecke, Bobenheim-Roxheim (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/910,554

(22) Filed: Jun. 5, 2013

(65) Prior Publication Data

US 2013/0331573 A1    Dec. 12, 2013

Related U.S. Application Data

(60) Provisional application No. 61/656,063, filed on Jun. 6, 2012.

(51) Int. Cl.
*C07D 295/023* (2006.01)
*C07D 241/04* (2006.01)
*C07C 209/28* (2006.01)
*C07C 213/04* (2006.01)
*C07D 295/027* (2006.01)

(52) U.S. Cl.
CPC ............ *C07D 241/04* (2013.01); *C07C 209/28* (2013.01); *C07C 213/04* (2013.01); *C07D 295/023* (2013.01); *C07D 295/027* (2013.01)
USPC ........................................................ 544/358

(58) Field of Classification Search
CPC .................................................. C07D 295/023
See application file for complete search history.

(56) References Cited

U.S. PATENT DOCUMENTS

| | | |
|---|---|---|
| 3,166,558 A | 1/1965 | Mascioli |
| 3,275,554 A | 9/1966 | Wagenaar |
| 3,751,475 A | 8/1973 | van der Voort et al. |
| 3,997,368 A | 12/1976 | Petroff et al. |
| 4,014,933 A | 3/1977 | Boettger et al. |
| 4,323,550 A | 4/1982 | Goupil |
| 4,442,306 A | 4/1984 | Mueller et al. |
| 4,739,051 A | 4/1988 | Schroeder et al. |
| 4,832,702 A | 5/1989 | Kummer et al. |
| 4,845,218 A | 7/1989 | Schroeder |
| 4,851,578 A | 7/1989 | Fischer et al. |
| 4,851,580 A | 7/1989 | Mueller et al. |
| 4,910,304 A | 3/1990 | Fischer et al. |
| 5,002,922 A | 3/1991 | Irgang et al. |
| 5,110,928 A | 5/1992 | Schroeder et al. |
| 5,463,130 A | 10/1995 | Witzel et al. |
| 5,530,127 A | 6/1996 | Reif et al. |
| 5,847,131 A | 12/1998 | Simon et al. |
| 6,057,442 A * | 5/2000 | Wulff-Doring et al. ...... 544/106 |
| 6,187,957 B1 | 2/2001 | Meyer et al. |
| 6,448,457 B1 | 9/2002 | Hesse et al. |
| 7,750,189 B2 * | 7/2010 | Kubanek et al. ............. 564/480 |
| 8,063,252 B2 * | 11/2011 | Hoffer et al. ................. 564/480 |

(Continued)

FOREIGN PATENT DOCUMENTS

| | | |
|---|---|---|
| CA | 1046166 A1 | 1/1979 |
| CA | 1055677 A1 | 6/1979 |

(Continued)

OTHER PUBLICATIONS

English-Language Translation of International Search Report for PCT/EP2013/061104, Oct. 4, 2013.
International Search Report and Written Opinion for PCT/EP2013/061104, Oct. 4, 2013.
U.S. Appl. No. 13/910,602, filed Jun. 5, 2013.
U.S. Appl. No. 13/906,960, filed May 31, 2013.
U.S. Appl. No. 13/906,931, filed May 31, 2013.
Database WPI, Week 198731, Thomson Scientific, London, GA; AN 1987-218358 (XP002664153), & JP 62 145076 A (KOA Corp) Jun. 29, 1987.

(Continued)

*Primary Examiner* — Andrew D Kosar
*Assistant Examiner* — John S Kenyon
(74) *Attorney, Agent, or Firm* — Drinker Biddle & Reath LLP

(57) ABSTRACT

Process for preparing piperazine of the formula I

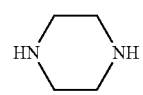
(I)

by reacting diethanolamine (DEOA) of the formula II

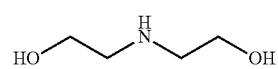
(II)

with ammonia in the presence of hydrogen and a supported, metal-containing catalyst has been found, wherein the catalytically active mass of the catalyst, prior to its reduction with hydrogen, comprises oxygen-containing compounds of aluminum, copper, nickel and cobalt and in the range from 0.2 to 5.0% by weight of oxygen-containing compounds of tin, calculated as SnO, and the reaction is carried out in the liquid phase at an absolute pressure in the range from 160 to 220 bar, a temperature in the range from 180 to 220° C., using ammonia in a molar ratio to DEOA used of from 5 to 25 and in the presence of 0.2 to 9.0% by weight of hydrogen, based on the total amount of DEOA used and ammonia.

34 Claims, 2 Drawing Sheets

(56) References Cited

U.S. PATENT DOCUMENTS

| | | |
|---|---|---|
| 8,436,169 B2 | 5/2013 | Wigbers et al. |
| 8,450,530 B2 | 5/2013 | Mueller et al. |
| 2003/0089591 A1 | 5/2003 | Wolfert et al. |
| 2005/0000791 A1 | 1/2005 | Wolfert et al. |
| 2007/0232833 A1 | 10/2007 | Haese et al. |
| 2008/0064882 A1 | 3/2008 | Huber-Dirr et al. |
| 2008/0255351 A1 | 10/2008 | Hoffer et al. |
| 2008/0299390 A1 | 12/2008 | Houssin et al. |
| 2009/0286977 A1 | 11/2009 | Kubanek et al. |
| 2010/0274010 A1 | 10/2010 | Kubanek et al. |
| 2010/0274055 A1 | 10/2010 | Kubanek et al. |
| 2011/0054167 A1 | 3/2011 | Kubanek et al. |
| 2011/0137029 A1 | 6/2011 | Kubanek et al. |
| 2011/0137030 A1 | 6/2011 | Kubanek et al. |
| 2011/0172430 A1 | 7/2011 | Ernst et al. |
| 2011/0218270 A1 | 9/2011 | Suter et al. |
| 2011/0218323 A1 | 9/2011 | Dahmen et al. |
| 2011/0251433 A1 | 10/2011 | Wigbers et al. |
| 2011/0251434 A1 | 10/2011 | Muller et al. |
| 2011/0288337 A1 | 11/2011 | Chedid et al. |
| 2011/0288338 A1 | 11/2011 | Wigbers et al. |
| 2011/0294977 A1 | 12/2011 | Schaub et al. |
| 2012/0035049 A1 | 2/2012 | Kubanek et al. |
| 2012/0035399 A1 | 2/2012 | Abillard et al. |
| 2012/0095221 A1 | 4/2012 | Wigbers et al. |
| 2012/0108816 A1 | 5/2012 | Wigbers et al. |
| 2012/0157679 A1 | 6/2012 | Wigbers et al. |

FOREIGN PATENT DOCUMENTS

| | | |
|---|---|---|
| CA | 2801109 A1 | 12/2011 |
| CN | 102101847 A | 6/2011 |
| CN | 102304101 A | 1/2012 |
| DE | 917 784 C | 9/1954 |
| DE | 941 909 C | 4/1956 |
| DE | 1954546 A1 | 5/1971 |
| DE | 21 25039 A1 | 12/1971 |
| DE | 1953263 A1 | 2/1972 |
| DE | 2445303 A1 | 4/1976 |
| DE | 26 28 087 A1 | 1/1977 |
| DE | 2706826 A1 | 9/1977 |
| DE | 36 11 230 A1 | 10/1987 |
| DE | 4021230 | 1/1991 |
| DE | 4028295 A1 | 3/1992 |
| DE | 19809418 A1 | 9/1999 |
| DE | 19859776 A1 | 6/2000 |
| DE | 10218849 A1 | 11/2003 |
| EP | 70 512 A1 | 1/1983 |
| EP | 75940 A1 | 4/1983 |
| EP | 0137478 A2 | 4/1985 |
| EP | 0227904 A1 | 7/1987 |
| EP | 235651 A1 | 9/1987 |
| EP | 0257443 A1 | 3/1988 |
| EP | 382049 A1 | 8/1990 |
| EP | 0434062 A1 | 6/1991 |
| EP | 440829 A1 | 8/1991 |
| EP | 446783 A2 | 9/1991 |
| EP | 514 692 A2 | 11/1992 |
| EP | 552 463 A1 | 7/1993 |
| EP | 599 180 A1 | 6/1994 |
| EP | 673 918 A1 | 9/1995 |
| EP | S696572 A1 | 2/1996 |
| EP | 0816350 A1 | 1/1998 |
| EP | 1 312 599 A1 | 5/2003 |
| EP | 1 312 600 A1 | 5/2003 |
| GB | 1512797 A | 6/1978 |
| JP | 62145076 A | 6/1987 |
| WO | WO-92/04119 A1 | 3/1992 |
| WO | WO-03/051508 A1 | 6/2003 |
| WO | WO-2004/085356 A1 | 10/2004 |
| WO | WO-2005/110969 A1 | 11/2005 |
| WO | WO-2006/005505 A1 | 1/2006 |
| WO | WO-2006/114417 A2 | 11/2006 |
| WO | WO-2007/036496 A1 | 4/2007 |
| WO | WO-2008/006750 A1 | 1/2008 |
| WO | WO-2008/006754 A1 | 1/2008 |
| WO | WO-2009/027249 A2 | 3/2009 |
| WO | WO-2009/080507 A1 | 7/2009 |
| WO | WO-2009/080508 A1 | 7/2009 |
| WO | WO-2009080506 A1 | 7/2009 |
| WO | WO-2009080507 A1 | 7/2009 |
| WO | WO-2009080508 A1 | 7/2009 |
| WO | WO-2010/031719 A1 | 3/2010 |
| WO | WO-2010/052181 A2 | 5/2010 |
| WO | WO-2010/054988 A2 | 5/2010 |
| WO | WO-2010/069856 A1 | 6/2010 |
| WO | WO-2010/089265 A2 | 8/2010 |
| WO | WO-2010/089266 A2 | 8/2010 |
| WO | WO-2010/089346 A2 | 8/2010 |
| WO | WO-2010/103062 A1 | 9/2010 |
| WO | WO-2010/106133 A1 | 9/2010 |
| WO | WO-2010/115759 A2 | 10/2010 |
| WO | WO-2010115759 A2 | 10/2010 |
| WO | WO-2010/146009 A1 | 12/2010 |
| WO | WO-2011/067200 A1 | 6/2011 |
| WO | WO-2011067199 A1 | 6/2011 |
| WO | WO-2011/082967 A1 | 7/2011 |
| WO | WO-2011/082994 A1 | 7/2011 |
| WO | WO-2011/107512 A1 | 9/2011 |
| WO | WO-2011/115759 A1 | 9/2011 |
| WO | WO-2011115759 A1 | 9/2011 |
| WO | WO-2011151268 A1 | 12/2011 |
| WO | WO-2011157710 A1 | 12/2011 |
| WO | WO-2012000952 A1 | 1/2012 |
| WO | WO-2012013563 A1 | 2/2012 |
| WO | WO-2012/049101 A1 | 4/2012 |
| WO | WO-2012049101 A1 | 4/2012 |
| WO | WO-2012055893 A1 | 5/2012 |
| WO | WO-2012080409 A1 | 6/2012 |
| WO | WO-2012/126956 A1 | 9/2012 |
| WO | WO-2012119927 A1 | 9/2012 |
| WO | WO-2012119928 A1 | 9/2012 |
| WO | WO-2012119929 A1 | 9/2012 |
| WO | WO-2012119930 A1 | 9/2012 |
| WO | WO-2012126869 A1 | 9/2012 |
| WO | WO-2013/030023 A1 | 3/2013 |
| WO | WO-2013/030287 A1 | 3/2013 |
| WO | WO-2013030143 A1 | 3/2013 |
| WO | WO-2013030144 A1 | 3/2013 |
| WO | WO-2013030161 A1 | 3/2013 |
| WO | WO-2013030172 A1 | 3/2013 |
| WO | WO-2013030174 A1 | 3/2013 |
| WO | WO-2013030249 A1 | 3/2013 |
| WO | WO-2013030254 A1 | 3/2013 |
| WO | WO-2013030255 A1 | 3/2013 |
| WO | WO-2013030258 A1 | 3/2013 |
| WO | WO-2013030259 A1 | 3/2013 |
| WO | WO-2013075974 A1 | 5/2013 |

OTHER PUBLICATIONS

International Search Report for PCT/EP2011/059848—Jun. 14, 2011, dated Jul. 25, 2011.
International Search Report for PCT/EP2011/067612 dated Nov. 22, 2011.
International Search Report for PCT/EP2011/068700, mailed Feb. 17, 2012.
U.S. Appl. No. 61/116,915, filed Nov. 21, 2008.
U.S. Appl. No. 61/354,753, filed Jun. 15, 2010.
U.S. Appl. No. 61/359,846, filed Jun. 30, 2010.
U.S. Appl. No. 61/368,656, filed Jul. 29, 2010.
U.S. Appl. No. 61/383,754, filed Sep. 17, 2010.
U.S. Appl. No. 61/407,467, filed Oct. 28, 2010.
U.S. Appl. No. 61/424,081, filed Dec. 17, 2010.
U.S. Appl. No. 61/450,157, filed Mar. 8, 2011.
U.S. Appl. No. 61/466,016, filed Mar. 22, 2011.
U.S. Appl. No. 61/392,960, filed Oct. 14, 2010.
U.S. Appl. No. 13/116,649, filed May 26, 2011.
U.S. Appl. No. 13/158,667, Jun. 13, 2011, Wigbers et al.
U.S. Appl. No. 13/173,437, filed Jun. 30, 2011, Huyghe et al.
U.S. Appl. No. 13/191,963, filed Jul. 27, 2011.
U.S. Appl. No. 12/234,328, filed Sep. 19, 2008.

(56) References Cited

OTHER PUBLICATIONS

U.S. Appl. No. 13/328,230, filed Dec. 16, 2011.
U.S. Appl. No. 13/415,466, filed Mar. 8, 2012.
U.S. Appl. No. 13/427,388, filed Mar. 22, 2012.
U.S. Appl. No. 61/450,147, filed Mar. 8, 2011.
U.S. Appl. No. 61/450,156, filed Mar. 8, 2011.
U.S. Appl. No. 61/450,161, filed Mar. 8, 2011.
U.S. Appl. No. 61/466,018, filed Mar. 22, 2011.
U.S. Appl. No. 61/487,306, filed May 18, 2011.
U.S. Appl. No. 61/527,149, filed Aug. 25, 2011.
U.S. Appl. No. 61/529,280, filed Aug. 31, 2011.
U.S. Appl. No. 61/529,282, filed Aug. 31, 2011.
U.S. Appl. No. 61/561,953, filed Nov. 21, 2011.
U.S. Appl. No. 61/585,253, filed Jan. 11, 2012.
U.S. Appl. No. 13/415,174, filed Mar. 8, 2012.
U.S. Appl. No. 13/415,409, filed Mar. 8, 2012.
U.S. Appl. No. 13/415,412, filed Mar. 8, 2012.
U.S. Appl. No. 13/427,308, filed Mar. 22, 2012.
U.S. Appl. No. 13/474,261, filed May 17, 2012.
U.S. Appl. No. 13/598,750, filed Aug. 30, 2012.
U.S. Appl. No. 13/599,325, filed Aug. 30, 2012.
U.S. Appl. No. 13/682,059, filed Nov. 20, 2012.
U.S. Appl. No. 13/737,158, filed Jan. 9, 2013.
U.S. Appl. No. 61/529,290, filed Aug. 31, 2011.
U.S. Appl. No. 61/529,291, filed Aug. 31, 2011.
U.S. Appl. No. 61/529,293, filed Aug. 31, 2011.
U.S. Appl. No. 61/529,295, filed Aug. 31, 2011.
U.S. Appl. No. 61/529,298, filed Aug. 31, 2011.
U.S. Appl. No. 61/529,303, filed Aug. 31, 2011.
U.S. Appl. No. 61/529,305, filed Aug. 31, 2011.
U.S. Appl. No. 61/529,308, filed Aug. 31, 2011.
U.S. Appl. No. 61/529,311, filed Aug. 31, 2011.
U.S. Appl. No. 61/529,338, filed Aug. 31, 2011.
U.S. Appl. No. 13/598,685, filed Aug. 30, 2012.
U.S. Appl. No. 13/598,691, filed Aug. 30, 2012.
U.S. Appl. No. 13/598,712, filed Aug. 30, 2012.
U.S. Appl. No. 13/598,715, filed Aug. 30, 2012.
U.S. Appl. No. 13/598,769, filed Aug. 30, 2012.
U.S. Appl. No. 13/599,270, filed Aug. 30, 2012.
U.S. Appl. No. 13/600,662, filed Aug. 31, 2012.
U.S. Appl. No. 13/600,848, filed Aug. 31, 2012.
U.S. Appl. No. 13/600,877, filed Aug. 31, 2012.
U.S. Appl. No. 61/529,314, filed Aug. 31, 2011.
U.S. Appl. No. 61/577,134, filed Nov. 8, 2011.
U.S. Appl. No. 61/654,130, filed Jun. 1, 2012.
U.S. Appl. No. 61/654,132, filed Jun. 1, 2012.
U.S. Appl. No. 61/656,053, filed Jun. 6, 2012.
U.S. Appl. No. 61/671,121, filed Jul. 13, 2012.
U.S. Appl. No. 61/674,423, filed Jul. 23, 2012.
U.S. Appl. No. 61/770,359, filed Feb. 28, 2013.
U.S. Appl. No. 13/167,959, filed Jun. 24, 2011.
U.S. Appl. No. 13/598,698, filed Aug. 30, 2012.
U.S. Appl. No. 13/720,027, filed Dec. 19, 2012.
U.S. Appl. No. 13/273,784, filed Oct. 14, 2011.
U.S. Appl. No. 61/407,936, filed Oct. 29, 2010.

\* cited by examiner

PROCESS FOR PREPARING PIPERAZINE

CROSS-REFERENCE TO RELATED APPLICATIONS

This application claims benefit (under 35 U.S.C. §119(e)) of U.S. Provisional Application 61/656,063, filed Jun. 6, 2012, which is incorporated herein by reference in its entirety.

BACKGROUND OF THE INVENTION

The present invention relates to a process for preparing piperazine of the formula I

by reacting diethanolamine (DEOA) of the formula II

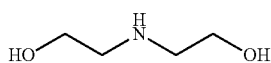

with ammonia in the presence of hydrogen and a supported, metal-containing catalyst.

Piperazine is used inter alia as an intermediate in the production of fuel additives (U.S. Pat. No. 3,275,554 A; DE 21 25 039 A and DE 36 11 230 A), surfactants, medicaments and crop protection compositions, hardeners for epoxy resins, catalysts for polyurethanes, intermediates for producing quaternary ammonium compounds, plasticizers, corrosion inhibitors, synthetic resins, ion exchangers, textile auxiliaries, dyes, vulcanization accelerators and/or emulsifiers.

WO 03/051508 A1 (Huntsman Petrochemical Corp.) relates to processes for the amination of alcohols using specific Cu/Ni/Zr/Sn-containing catalysts which, in a further embodiment, comprise Cr instead of Zr (see page 4, lines 10-16). The catalysts described in this WO application comprise no aluminum oxide and no cobalt.

WO 2008/006750 A1 (BASF AG) relates to certain Pb, Bi, Sn, Sb and/or In-doped, zirconium dioxide-, copper-, nickel- and cobalt-containing catalysts and their use in processes for preparing an amine by reacting a primary or secondary alcohol, aldehyde and/or ketone with hydrogen and ammonia, a primary or secondary amine. Aluminum oxide supports are not taught.

WO 2009/080507 A1 (BASF SE) describes certain Sn and Co-doped, zirconium dioxide-, copper- and nickel-containing catalysts and their use in processes for preparing an amine by reacting a primary or secondary alcohol, aldehyde and/or ketone with hydrogen and ammonia, a primary or secondary amine. Aluminum oxide supports are not taught.

WO 2009/080506 A1 (BASF SE) describes certain Pb, Bi, Sn, Mo, Sb and/or P-doped, zirconium dioxide-, nickel- and iron-containing catalysts and their use in processes for preparing an amine by reacting a primary or secondary alcohol, aldehyde and/or ketone with hydrogen and ammonia, a primary or secondary amine. Aluminum oxide supports are not taught. Preferably, the catalysts comprise no Cu and no Co.

WO 2009/080508 A1 (BASF SE) teaches certain Pb, Bi, Sn and/or Sb-doped, zirconium dioxide-, copper-, nickel-, cobalt- and iron-containing catalysts and their use in processes for preparing an amine by reacting a primary or secondary alcohol, aldehyde and/or ketone with hydrogen and ammonia, a primary or secondary amine. Aluminum oxide supports are not taught.

WO 2011/067199 A1 (BASF SE) relates to certain aluminum oxide-, copper-, nickel-, cobalt- and tin-containing catalysts and their use in processes for preparing an amine from a primary or secondary alcohol, aldehyde and/or ketone. The preparation of piperazine from DEOA and ammonia is mentioned generally on page 22, line 28.

WO 2011/157710 A1 (BASF SE) describes the preparation of certain cyclic tertiary methylamines, where an aminoalcohol from the group 1,4-aminobutanol, 1,5-aminopentanol, aminodiglycol (ADG) or aminoethylethanolamine, is reacted with methanol at elevated temperature in the presence of a copper-containing heterogeneous catalyst in the liquid phase.

WO 2012/049101 A1 (BASF SE) relates to a process for preparing certain cyclic tertiary amines by reacting an aminoalcohol from the group 1,4-aminobutanol, 1,5-aminopentanol, aminodiglycol (ADG) or aminoethylethanolamine with a certain primary or secondary alcohol at elevated temperature in the presence of a copper-containing heterogeneous catalyst in the liquid phase.

CN 102 304 101 A (Shaoxing Xingxin Chem. Co., Ltd.) relates to the simultaneous preparation of piperazine and N-alkylpiperazines by reacting N-hydroxyethyl-1,2-ethanediamine with primary $C_{1-7}$-alcohols in the presence of metallic catalysts.

DE 198 59 776 A1 (BASF AG) relates to certain amination processes using catalyst moldings which comprise oxygen-containing compounds of titanium and of copper and metallic copper.

BRIEF SUMMARY OF THE INVENTION

Figure 1:
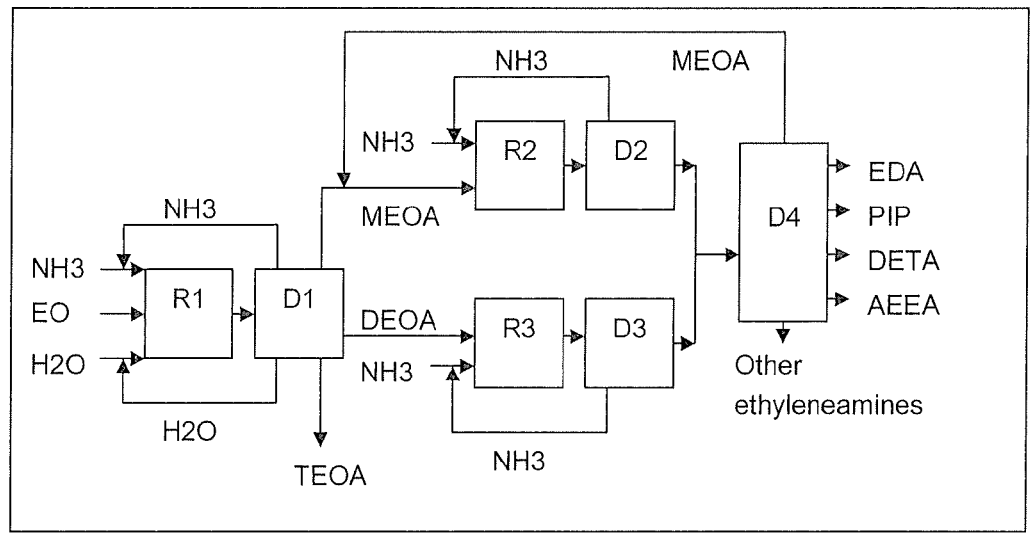
FIG. 1 schematically shows a particularly preferred embodiment of the integrated process.

The object of the present invention was to improve the economic feasibility of processes to date for the preparation of piperazine of the formula I and to overcome one or more disadvantages of the prior art. The aim was to find conditions which can be established in technical terms in a simple manner and which make it possible to carry out the process with high conversion, high yield, space-time yields (STY), selectivity coupled with simultaneously high mechanical stability of the catalyst molding and low "runaway risk".

[Space-time yields are given in "amount of product/(catalyst volume·time)" (kg/($I_{cat.}$·h)) and/or "amount of product/(reactor volume·time)" (kg/($I_{reactor}$·h)].

A DETAILED DESCRIPTION OF THE INVENTION

Accordingly, a process for the preparation of piperazine of the formula I

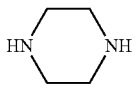

(I)

by reacting diethanolamine (DEOA) of the formula II

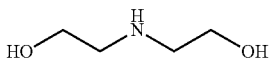

(II)

with ammonia in the presence of hydrogen and a supported, metal-containing catalyst has been found, wherein the catalytically active mass of the catalyst, prior to its reduction with hydrogen, comprises oxygen-containing compounds of aluminum, copper, nickel and cobalt and in the range from 0.2 to 5.0% by weight of oxygen-containing compounds of tin, calculated as SnO, and the reaction is carried out in the liquid phase at an absolute pressure in the range from 160 to 220 bar, a temperature in the range from 180 to 220° C., using ammonia in a molar ratio to DEOA used of from 5 to 25 and in the presence of 0.2 to 9.0% by weight of hydrogen, based on the total amount of DEOA used and ammonia.

In particular, catalysts whose catalytically active mass prior to their reduction with hydrogen, comprises in the range from
15 to 80% by weight of oxygen-containing compounds of aluminum, calculated as $Al_2O_3$,
1 to 20% by weight of oxygen-containing compounds of copper, calculated as CuO,
5 to 35% by weight of oxygen-containing compounds of nickel, calculated as NiO,
5 to 35% by weight of oxygen-containing compounds of cobalt, calculated as CoO, and
0.2 to 5.0% by weight of oxygen-containing compounds of tin, calculated as SnO,
are used in the aforementioned amination process.

The process can be carried out continuously or discontinuously. Preference is given to a continuous procedure.

In the circulating-gas procedure, the starting materials (DEOA, ammonia) are evaporated in a circulating-gas stream and passed to the reactor in gaseous form.

The starting materials (DEOA, ammonia) can also be evaporated as aqueous solutions and be passed with the circulating-gas stream to the catalyst bed.

Preferred reactors are tubular reactors. Examples of suitable reactors with circulating-gas stream can be found in Ullmann's Encyclopedia of Industrial Chemistry, 5th Ed., Vol. B 4, pages 199-238, "Fixed-Bed Reactors".

Alternatively, the reaction takes place advantageously in a tube-bundle reactor or in a mono-stream plant.

In a mono-stream plant, the tubular reactor in which the reaction takes place can consist of a serial connection of a plurality (e.g. two or three) of individual tubular reactors. Optionally, an intermediate introduction of feed (comprising the DEOA and/or ammonia and/or $H_2$) and/or circulating gas and/or reactor discharge from a downstream reactor is advantageously possible here.

The circulating-gas amount is preferably in the range from 40 to 1500 m³ (at atmospheric pressure)/[m³ of catalyst (bed volume)·h], in particular in the range from 60 to 750 m³ (at atmospheric pressure)/[m³ of catalyst (bed volume)·h], further particularly preferably in the range from 100 to 400 m³ (at atmospheric pressure)/[m³ of catalyst (bed volume)·h]. (Atmospheric pressure=1 bar abs.)

The circulating gas comprises preferably at least 10, particularly 50 to 100, very particularly 80 to 100, % by volume of $H_2$.

In the process according to the invention, the catalysts are used preferably in the form of catalysts which consist only of catalytically active mass and optionally a shaping auxiliary (such as e.g. graphite or stearic acid), if the catalyst is used as moldings, i.e. comprise no further catalytically active accompanying substances.

In this connection, the oxidic support material aluminum oxide ($Al_2O_3$) is deemed as belonging to the catalytically active mass.

The catalysts are used by introducing the catalytically active mass ground to powder into the reaction vessel, or by arranging the catalytically active mass after grinding, mixing with shaping auxiliaries, shaping and heat-treating as catalyst moldings—for example as tablets, beads, rings, extrudates (e.g. strands)—in the reactor.

The concentration data (in % by weight) of the components of the catalyst refer in each case—unless stated otherwise— to the catalytically active mass of the finished catalyst after its last heat treatment and before its reduction with hydrogen.

The catalytically active mass of the catalyst, after its last heat treatment and before its reduction with hydrogen, is defined as the sum of the masses of the catalytically active constituents and of the aforementioned catalyst support materials and comprises essentially the following constituents: aluminum oxide ($Al_2O_3$), oxygen-containing compounds of copper, nickel and cobalt and oxygen-containing compounds of tin.

The sum of the aforementioned constituents of the catalytically active mass is usually 70 to 100% by weight, preferably 80 to 100% by weight, particularly preferably 90 to 100% by weight, particularly >95% by weight, very particularly >98% by weight, in particular >99% by weight, e.g. particularly preferably 100% by weight.

The catalytically active mass of the catalysts according to the invention and used in the process according to the invention can further comprise one or more elements (oxidation state 0) or inorganic or organic compounds thereof selected from groups IA to VI A and IB to VII B and VIII of the Periodic Table of the Elements.

Examples of such elements and their compounds are: transition metals, such as Mn and $MnO_2$, W and tungsten oxides, Ta and tantalum oxides, Nb and niobium oxides or niobium oxalate, V and vanadium oxides and vanadyl pyrophosphate; lanthanides, such as Ce and $CeO_2$ or Pr and $Pr_2O_3$; alkaline earth metal oxides, such as SrO; alkaline earth metal carbonates, such as $MgCO_3$, $CaCO_3$ and $BaCO_3$; boron oxide ($B_2O_3$).

Preferably, the catalytically active mass of the catalysts according to the invention and catalysts used in the process according to the invention comprises no rhenium, no ruthenium, no iron and/or no zinc, in each case neither in metallic (oxidation state=0) nor in an ionic (oxidation state≠0), in particular oxidized, form.

Preferably, the catalytically active mass of the catalysts according to the invention and catalysts used in the process according to the invention comprises no silver and/or molybdenum, in each case neither in metallic (oxidation state=0) nor in an ionic (oxidation state≠0), in particular oxidized, form.

In a particularly preferred embodiment, the catalytically active mass of the catalysts according to the invention and catalysts used in the process according to the invention comprises no further catalytically active component, neither in elemental (oxidation state=0) nor in ionic (oxidation state≠0) form.

In the particularly preferred embodiment, the catalytically active mass is not doped with further metals or metal compounds.

However, customary accompanying trace elements originating from the metal extraction of Cu, Co, Ni, Sn are excluded from this.

Preferably, the catalytically active mass of the catalyst comprises no oxygen-containing compounds of silicon and/or of zirconium.

Preferably, the catalytically active mass of the catalyst comprises no oxygen-containing compounds of titanium and/or of chromium.

The catalytically active mass of the catalyst comprises, prior to its reduction with hydrogen, in the range from 0.2 to 5.0% by weight, particularly in the range from 0.4 to 4.0% by weight, further particularly in the range from 0.6 to 3.0% by weight, further particularly preferably in the range from 0.7 to 2.5% by weight, of oxygen-containing compounds of tin, calculated as SnO.

The catalytically active mass of the catalyst comprises, prior to its reduction with hydrogen, preferably in the range from 5.0 to 35% by weight, particularly in the range from 10 to 30% by weight, further particularly in the range from 12 to 28% by weight, very particularly 15 to 25% by weight, of oxygen-containing compounds of cobalt, calculated as CoO.

The catalytically active mass of the catalyst comprises, prior to its reduction with hydrogen, furthermore preferably in the range from
15 to 80% by weight, particularly 30 to 70% by weight, further particularly 35 to 65% by weight, of oxygen-containing compounds of aluminum, in each case calculated as $Al_2O_3$,
1 to 20% by weight, particularly 2 to 18% by weight, further particularly 5 to 15% by weight, of oxygen-containing compounds of copper, in each case calculated as CuO, and
5 to 35% by weight, particularly 10 to 30% by weight, further particularly 12 to 28% by weight, very particularly 15 to 25% by weight, of oxygen-containing compounds of nickel, in each case calculated as NiO.

The molar ratio of nickel to copper is preferably greater than 1, particularly preferably greater than 1.2, further particularly preferably in the range from 1.8 to 8.5.

The BET surface area (ISO 9277:1995) of the catalysts according to the invention and catalysts used in the process according to the invention is preferably in the range from 30 to 250 $m^2/g$, particularly in the range from 90 to 200 $m^2/g$, further particularly in the range from 130 to 190 $m^2/g$ (in each case prior to the reduction with hydrogen). These ranges are attained in particular by calcination temperatures during catalyst production in the range from 400 to 600° C., particularly 420 to 550° C. (cf. below).

Various methods are possible for producing the catalysts used in the process according to the invention. They are obtainable, for example, by peptization of pulverulent mixtures of the hydroxides, carbonates, oxides and/or other salts of the components with water and subsequent extrusion and heating (heat treatment) of the mass obtained in this way.

Preference is given to using precipitation methods for producing the catalysts according to the invention. Thus, they can be obtained for example as a result of a common precipitation of the nickel, cobalt, copper and Sn components from an aqueous salt solution comprising these elements by means of bases in the presence of a slurry of a sparingly soluble, oxygen-containing aluminum compound and subsequent washing, drying and calcination of the resulting precipitate. Sparingly soluble, oxygen-containing aluminum compounds which can be used are, for example, aluminum oxide, aluminum oxide hydrate, aluminum phosphates, borates and silicates. The slurries of the sparingly soluble aluminum compounds can be produced by suspending finely particulate powders of these compounds in water with vigorous stirring. These slurries are advantageously obtained by precipitating the sparingly soluble aluminum compounds from aqueous aluminum salt solutions by means of bases.

Preferably, the catalysts according to the invention are prepared via a common precipitation (mixed precipitation) of all of their components. For this purpose, an aqueous salt solution comprising the catalyst components is expediently admixed, at elevated temperature and with stirring, with an aqueous base—for example sodium carbonate, sodium hydroxide, potassium carbonate or potassium hydroxide—until the precipitation is complete. It is also possible to work with alkali metal-free bases such as ammonia, ammonium carbonate, ammonium hydrogencarbonate, ammonium carbamate, ammonium oxalate, ammonium malonate, urotropin, urea, etc. The type of salts used is generally not critical: since what matters in this procedure is primarily the solubility of these salts in water, one criterion is their good water solubility required for producing these relatively highly concentrated salt solutions. It is considered self-evident that when selecting the salts of the individual components, naturally only salts will be selected whose anions do not lead to disturbances, whether by causing undesired precipitations or by hindering or preventing precipitation as a result of complexation.

The precipitates obtained in these precipitation reactions are generally chemically non-uniform and consist inter alia of mixtures of the oxides, oxide hydrates, hydroxides, carbonates and insoluble and basic salts of the metals used. It may prove to be favorable for the filterability of the precipitates if they are aged, i.e. if they are left to themselves for some time after the precipitation, optionally at elevated temperature or while passing air through.

The precipitates obtained by these precipitation methods are further processed in the conventional manner to give the catalysts according to the invention. Firstly, the precipitates are washed. The content of alkali metal which has been introduced as a result of the (mineral) base possibly used as precipitating agent can be influenced via the duration of the washing operation and via the temperature and amount of the wash water. In general, by extending the washing time or increasing the temperature of the wash water, the content of alkali metal will decrease. After the washing, the precipitated material is generally dried at 80 to 200° C., preferably at 100 to 150° C., and then calcined. The calcination is generally carried out at temperatures between 300 and 800° C., preferably at 400 to 600° C., in particular at 420 to 550° C.

The catalysts according to the invention can also be produced by impregnation of aluminum oxide ($Al_2O_3$), which is present for example in the form of powders or moldings, such as extrudates, tablets, beads or rings.

The aluminum oxide is used for example in the amorphous, gamma, theta and/or delta form, as aluminum oxohydroxide (boehmite), preferably in the amorphous form.

Moldings can be produced by customary methods.

The impregnation likewise takes place by customary methods, as described e.g. in A. B. Stiles, Catalyst Manufacture—Laboratory and Commercial Preparations, Marcel Dekker, New York (1983), by applying a corresponding metal salt solution in each case in one or more impregnation stages, where the metal salts used are e.g. corresponding nitrates, acetates or chlorides. After the impregnation, the mass is dried and optionally calcined.

The impregnation can take place by the so-called "incipient wetness" method in which the aluminum oxide is wetted according to its water absorption capacity at most up to saturation with the impregnation solution. However, impregnation can also take place in supernatant solution.

In the case of multistage impregnation methods, it is expedient to dry and optionally calcine between individual impregnation steps. Multistage impregnation is to be used advantageously particularly when the aluminum oxide is to be supplied with a relatively large amount of metal.

To apply the metal components to the aluminum oxide, the impregnation can take place simultaneously with all metal salts or in any desired order of the individual metal salts in succession.

Subsequently, the catalysts produced by impregnation are dried and preferably also calcined, e.g. at the calcination temperature ranges already stated above.

After the calcination, the catalyst is expediently conditioned, whether by adjusting it to a certain grain size by means of grinding, or mixing it after it has been ground with molding auxiliaries such as graphite or stearic acid, pressing using a press to give moldings, e.g. tablets, and heat-treating. The heat-treatment temperatures here preferably correspond to the temperatures during the calcination.

The catalysts produced in this way comprise the catalytically active metals in the form of a mixture of their oxygen-containing compounds, i.e. in particular as oxides and mixed oxides.

The catalysts produced e.g. as described above are stored and optionally treated as they are. Prior to being used as catalysts, they are conventionally pre-reduced. However, they can also be used without pre-reduction, in which case they are then reduced under the conditions of the hydrogenating amination by the hydrogen present in the reactor.

For the purposes of pre-reduction, the catalysts are exposed to a nitrogen/hydrogen atmosphere firstly at preferably from 150 to 200° C. over a period of e.g. 12 to 20 hours and subsequently treated in a hydrogen atmosphere for up to approx. 24 more hours at preferably 200 to 400° C. During this pre-reduction, some of the oxygen-containing metal compounds present in the catalysts are reduced to give the corresponding metals, meaning that these are present together with the different types of oxygen compounds in the active form of the catalyst.

The process according to the invention is preferably carried out continuously, the catalyst preferably being arranged as a fixed bed in the reactor. In this connection, flow through the fixed catalyst bed from above and also from below is possible.

The ammonia is used in a 5- to 25-fold molar amount, preferably 8- to 23-fold molar amount, further preferably 9- to 22-fold molar amount, particularly 10- to 21-fold molar amount, in particular in an 11- to 20-fold molar amount, e.g. 12- to 19-fold molar amount, in each case based on the DEOA used.

The ammonia can be used as aqueous solution, particularly as 30 to 90% strength by weight aqueous solution. It is preferably used without further solvent (compressed gas, purity particularly 95 to 100% strength by weight).

The starting material DEOA is preferably used as aqueous solution, particularly as 75 to 95% strength by weight aqueous solution, e.g. 80% strength by weight aqueous solution.

Preferably, an offgas amount of from 1 to 800 cubic meters (stp)/(cubic meters of catalyst·h), in particular 2 to 200 cubic meters (stp)/(m$^3$ of catalyst·h) is processed. [Cubic meters (stp) volume converted to standard temperature and pressure conditions (20° C., 1 bar abs.)]. Catalyst volume data always refers to the bulk volume.

The amination of the primary alcohol groups of the starting material DEOA is carried out in the liquid phase. Preferably, the fixed bed process is in the liquid phase.

When working in the liquid phase, the starting materials (DEOA, ammonia) are passed, preferably simultaneously, in liquid phase at pressures of from 16.0 to 22.0 MPa (160 to 220 bar), preferably 17.0 to 22.0 MPa, further preferably 18.0 to 21.0 MPa, further preferably 19.0 to 20.0 MPa, and temperatures of from 180 to 220° C., particularly 185 to 215° C., preferably 190 to 210° C., in particular 190 to 205° C., including hydrogen over the catalyst, which is usually located in a fixed-bed reactor heated preferably from the outside. Here, both a trickle mode and also a liquid-phase mode is possible. The catalyst hourly space velocity is generally in the range from 0.3 to 0.8, preferably 0.4 to 0.7, particularly preferably 0.5 to 0.6 kg, of DEOA per liter of catalyst (bed volume) and per hour (DEOA calculated as 100% strength). Optionally, the starting materials can be diluted with a suitable solvent, such as water, tetrahydrofuran, dioxane, N-methylpyrrolidone or ethylene glycol dimethyl ether. It is expedient to heat the reactants even before they are introduced into the reaction vessel, preferably to the reaction temperature.

The reaction is carried out in the presence of 0.2 to 9.0% by weight of hydrogen, particularly in the presence of 0.25 to 7.0% by weight of hydrogen, further particularly in the presence of 0.3 to 6.5% by weight of hydrogen, very particularly in the presence of 0.4 to 6.0% by weight of hydrogen, in each case based on the total amount of DEOA used and ammonia.

The pressure in the reaction vessel which arises from the sum of the partial pressures of the ammonia, of the DEOA and of the reaction products formed, and also optionally of the co-used solvent at the stated temperatures, is expediently increased to the desired reaction pressure by injecting hydrogen.

In the case of continuous operation in the liquid phase, the excess ammonia can be circulated together with the hydrogen.

If the catalyst is arranged as a fixed bed, it can be advantageous for the selectivity of the reaction to mix the catalyst moldings in the reactor with inert packings, to "dilute" them so to speak. The fraction of the packings in such catalyst preparations can be 20 to 80, particularly 30 to 60 and in particular 40 to 50, parts by volume.

The water of reaction formed in the course of the reaction (in each case one mole per mole of reacted alcohol group) generally does not have a disruptive effect on the degree of conversion, the rate of reaction, the selectivity and the service life of the catalyst and is therefore expediently only removed upon work-up of the reaction mixture, e.g. by distillation.

After the reaction discharge has expediently been decompressed, the excess hydrogen and the optionally present excess aminating agents are removed therefrom and the crude reaction product obtained is purified, e.g. by means of fractional rectification. Suitable work-up methods are described e.g. in EP 1 312 600 A and EP 1 312 599 A (both BASF AG). The excess ammonia and the hydrogen are advantageously returned again to the reaction zone. The same applies for any incompletely reacted DEOA.

A work-up of the product of the reaction is preferably as follows:

From the reaction product of the reaction, by means of distillation, (i) firstly unreacted ammonia is separated off overhead,
(ii) water is separated off overhead,
(iii) optionally present by-products with a lower boiling point than that of the process product I (low boilers) are separated off overhead,
(iv) the process product piperazine (I) is separated off overhead, with optionally present by-products with a higher boiling point than that of the process product I (high boilers) and optionally present unreacted DEOA (II) remaining in the bottom.

During the reaction of the process according to the invention, the aminoethylethanolamine (AEEA) of the formula III

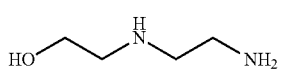

can be formed as by-product:

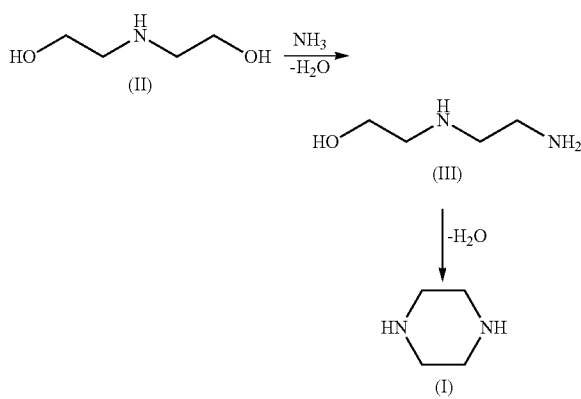

Therefore, in particular by means of distillation,
(v) from the bottom of step iv, optionally present unreacted DEOA (II) and/or optionally present aminoethylethanolamine as by-product with the formula III are separated off overhead and returned to the reaction.

Ammonia separated off in step i and having a purity of from 90 to 99.9% by weight, particularly 95 to 99.9% by weight, is preferably returned to the reaction, in which case some of the separated-off ammonia, particularly 1 to 30% by weight of the separated-off ammonia, further particularly 2 to 20% by weight of the separated-off ammonia, can be removed.

In one particular embodiment, the invention relates to an integrated, multistage process for preparing piperazine, 1,2-ethylenediamine (EDA), diethylenetriamine (N-(2-aminoethyl)-1,2-ethylenediamine, DETA) and N-(2-aminoethyl)ethanolamine (AEEA), where (reaction stage 1=R1) in a first reaction stage ethylene oxide (EO) is reacted continuously with ammonia to give a product comprising monoethanolamine (MEOA), diethanolamine (DEOA) and triethanolamine (TEOA), distillation stage 1=D1) the ethanolamines MEOA, DEOA and TEOA are separated by distillation, (reaction stage 2=R2) MEOA separated off in D1, completely or partly, preferably completely, is continuously reacted with ammonia in a second reaction stage in the presence of an amination catalyst and (reaction stage 3=R3) DEOA separated off in D1, completely or partly, preferably completely, is reacted in a third reaction stage with ammonia by the process as described above.

Preferably, in the first reaction stage, ethylene oxide (EO) is reacted with ammonia in the presence of water as catalyst.

In particular, water and/or ammonia produced in distillation stage 1 (D1) is returned to the first reaction stage (R1).

The aminating catalyst used in the second reaction stage (R2) is preferably a Cu-containing heterogeneous catalyst, further preferably a Cu- and Ni-containing heterogeneous catalyst, particularly a Cu- and Ni- and Co-containing heterogeneous catalyst, very particularly the Cu/Ni/Co/Al$_2$O$_3$ catalyst disclosed in DE 19 53 263 A (BASF AG).

Furthermore, in an alternative embodiment, in the second reaction stage (R2), preference is given to using a Cu- and Ln-containing heterogeneous catalyst, particularly the Cu/Ln/Al$_2$O$_3$ catalyst taught in WO 2010/115759 A (BASF SE).

In reaction stage 3, particular preference is given to a procedure in which the DEOA is converted to at least 95%, particularly to 98 to 100%.

Preferably, ammonia present is separated off from the reaction product of reaction stage 2 by distillation (distillation stage 2=D2). Separated-off ammonia is advantageously returned to reaction stage 2.

Further preferably, ammonia present is separated off from the reaction product of reaction stage 3 (distillation stage 3=D3) by distillation. Separated-off ammonia is advantageously returned to reaction stage 3.

The two reaction products remaining after separating off the ammonia are preferably combined, and piperazine, EDA, DETA and AEEA and optionally present MEOA are separated off from the combined product (distillation stage 4=D4) by distillation.

In distillation stage 4 (D4), optionally present MEOA is advantageously returned to the second reaction stage (R2).

FIG. 1, accordingly, schematically shows a particularly preferred embodiment of the integrated process.

Alternatively, it is preferred to combine the reaction products from the two reaction stages R2 and R3, to separate off ammonia present from the combined product (distillation stage 3=D3) by distillation and then to separate off piperazine, EDA, DETA and AEEA and optionally present MEOA by distillation (distillation stage 4=D4).

Ammonia separated off in distillation stage 3 is advantageously returned to reaction stage 2 and/or 3.

MEOA optionally produced in distillation stage 4 (D4) is advantageously returned to the second reaction stage (R2).

Figure 2:
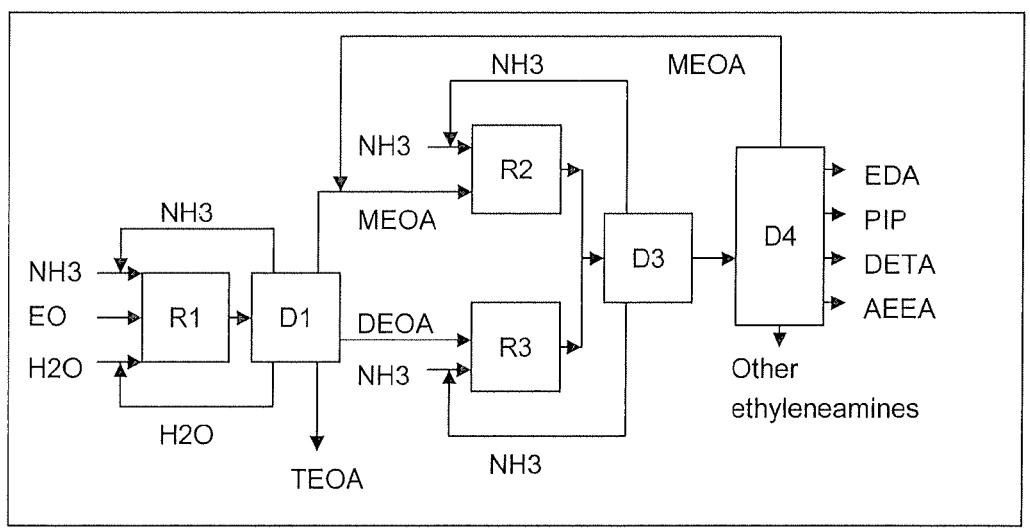
FIG. 2 shows in a diagram form, a further particularly preferred embodiment of the integrated process.

FIG. 2 accordingly shows, in diagram form, a further particularly preferred embodiment of the integrated process.

All pressure data refer to the absolute pressure.
All ppm data refer to the mass.

Examples

1. Preparation of Catalyst A [=Example 4 in WO 2011/067199 A (BASF SE)]

An aqueous solution of nickel nitrate, cobalt nitrate, copper nitrate, aluminum nitrate and tin(II) chloride which comprised 3.9% by weight of Ni, 3.9% by weight of Co, 1.9% by weight of Cu, 5.5% by weight of Al$_2$O$_3$ and 0.5% by weight of Sn was precipitated simultaneously in a stirred vessel in a constant stream with a 20% strength by weight aqueous sodium carbonate solution at a temperature of 65-70° C. such that the pH of 5.7, measured using a glass electrode, was maintained. After the precipitation, air was blown in for 1 hour, then the pH of the solution was adjusted to a value of 7.4 using sodium carbonate solution. The resulting suspension was filtered and the filtercake was washed with demineralized water until the electrical conductivity of the filtrate was ca. 20 mS. The filtercake was then dried at a temperature of 150° C. in a drying cabinet. The hydroxide carbonate mixture obtained in this way was then calcined at a temperature of 500° C. for 4 hours. The catalyst mass was then mixed with 3% by weight of graphite and molded to give tablets 3×3 mm.

ca. 185 to 200° C. and a total pressure of 190 or 200 bar. The reaction temperature was selected such that a DEOA conversion of >90% was reached. The mixture leaving the reactor was cooled and decompressed to atmospheric pressure. At various times, samples were taken from the reaction mixture and analyzed by means of gas chromatography. For this, an "RTX-5 amine" GC column 30 m in length was used, with a temperature program: 70° C./5 min., heat to 280° C. at a rate of 5° C./min., at 280° C./10 minutes.

The results of the experiments can be found in Table II below.

TABLE II

| Example 2 | Temp. ° C. | % by wt. of $H_2$ based on DEOA + $NH_3$ | HSV kg/ (l·h) 80% strength | MR | PIP % by wt. | DEOA % by wt. | EDA % by wt. | DETA % by wt. | AEEA % by wt. | AEPIP % by wt. | Amix % by wt. | $H_2O$ % by wt. | PIP sel. mol % | EA sel. mol % |
|---|---|---|---|---|---|---|---|---|---|---|---|---|---|---|
| A | 190 | 1.5 | 0.50 | 13 | 42.5 | 1.0 | 4.1 | 1.2 | 0.3 | 6.3 | 7.7 | 36.0 | 69.0 | 93.2 |
| B | 190 | 0.8 | 0.50 | 18 | 42.0 | 1.0 | 4.2 | 1.8 | 1.3 | 4.6 | 7.0 | 37.0 | 68.7 | 92.6 |
| C | 190 | 5.8 | 0.50 | 18 | 36.9 | 1.0 | 3.0 | 1.0 | 0.9 | 6.3 | 12.4 | 37.1 | 62.4 | 93.8 |
| D | 193 | 1.0 | 0.46 | 13 | 40.8 | 1.1 | 4.0 | 1.4 | 0.6 | 6.0 | 8.2 | 36.6 | 67.2 | 92.8 |

Pressure: 200 bar; in example 2A: 190 bar
Temp.: temperature in the reactor
HSV: catalyst hourly space velocity [kg of DEOA/(liter$_{cat.}$·h)]
MR: molar ratio of $NH_3$ to DEOA in the feed
Sel.: selectivity.
PIP sel. = piperazine selectivity;
EA sel. = selectivity of all ethyleneamines.
PIP: piperazine
AEPIP: N-(2-aminoethyl)piperazine
Amix: ethyleneamines with a higher boiling point than AEPIP The tablets obtained in this way are reduced in hydrogen at a temperature of 280-300° C. for at least 12 hours. The passivation of the reduced catalyst was carried out at room temperature in diluted air (air in $N_2$ with an $O_2$ content of at most 5% by volume). The catalyst obtained in this way had the composition as shown in Table I below.

TABLE I

| Catalyst *) | Ni % | Co % | Cu % | Sn % | BET **) $m^2/g$ | Support |
|---|---|---|---|---|---|---|
| catalyst A | 18.6 | 17.3 | 10.6 | 1.1 | 187 | $Al_2O_3$ |

*) Catalyst composition in % by weight; remainder up to 100% by weight is the support
**) ISO 9277:1995

2. Reaction of DEOA with Ammonia in a Continuously Operated Tubular Reactor

A heated tubular reactor with an internal diameter of 14 mm, a centrally installed thermocouple and a total volume of 1000 ml was filled in the lower section with a bed of glass beads (250 ml), on top of this 500 ml of the reduced catalyst A and finally the remainder was filled again with glass beads. Prior to the reaction, the catalyst was activated under atmospheric pressure for 24 hours at max. 280° C. under hydrogen (25 l (stp)/h)(l (stp)=liters at standard temperature and pressure=volume converted to standard temperature and pressure conditions (20° C., 1 bar abs.)). A certain amount of DEOA (80% strength aqueous), ammonia and hydrogen, as stated in Table II below, were metered through the reactor from bottom to top. The reactor was held at a temperature of The work-up can preferably take place by means of the following five steps:
1) Separating off unreacted ammonia and returning it to the reactor Optional removal of some of the ammonia from the top of the column.
2) Separating off water
3) Separating off low-boiling secondary components
4) Pure distillation of the piperazine (1) overhead while separating off high-boiling secondary components via the bottom.
5) Optionally returning some of the high-boiling secondary components, in particular diethanolamine, N-(2-aminoethyl)ethanolamine (AEEA), N-(2-aminoethyl)ethane-1,2-diamine (diethylenetriamine, DETA) to the reaction.

3. Preparation of Piperazine, 1,2-ethylenediamine (EDA), Diethylenetriamine (DETA) and N-(2-aminoethyl)ethanolamine (AEEA) (According to FIG. 1)

The reaction of EO with $NH_3$, homogeneously catalyzed with water, was carried out continuously at an $NH_3$:EO molar ratio (MR) of 10 (reaction stage 1).

In the process, 100 mol/h of EO produced 46.5 mol/h of MEOA, 18.7 mol/h of DEOA and 5.4 mol/h of TEOA (weight ratio: 62:29:9=MEOA:DEOA:TEOA).

The ethanolamines were separated off by distillation (distillation stage 1).

The complete amount of the MEOA was reacted in reaction stage 2 in a reactor in the presence of the Cu/Ni/Co/$Al_2O_3$ catalyst according to DE 19 53 263 A (BASF AG), therein Example 1 on page 5, with $NH_3$ (molar ratio of $NH_3$:MEOA=8:1) in the presence of 0.5% by weight of hydrogen based on the total amount of $NH_3$ and MEOA at 190° C. and a catalyst hourly space velocity of 0.6 kg of MEOA/($l_{cat.}$·h) to give ethyleneamines (in particular PIP, EDA, DETA, AEEA). The excess NH₃ was separated off in distillation stage D2 and returned to R2.

The complete amount of the DEOA was reacted in reaction stage 3 in a reactor in the presence of the Cu/Ni/Co/Sn Al₂O₃ catalyst A (see above) with NH₃ as in Example 2A (Table II) to give ethyleneamines (in particular PIP, EDA, DETA, AEEA). The excess NH₃ was separated off in distillation stage D3 and returned to R3.

The products from distillation stages 2 and 3 were brought together and the ethyleneamines were separated off by distillation (distillation stage 4). Unreacted MEOA was returned to R2. Formed in total in this process by the reaction of the total amount of the ethanol-amines MEOA and DEOA which were formed in reaction stage 1 (see above, 46.5 mol/h of MEOA and 18.7 mol/h of DEOA) and were separated off in distillation stage 1, were:

From 46.5 mol/h of MEOA: 28.83 mol/h of EDA, 3.26 mol/h of PIP, 2.56 mol/h of DETA and 2.33 mol/h of AEEA.

From 18.7 mol/h of DEOA: 12.9 mol/h of PIP, 2.5 mol/h of EDA, 0.4 mol/h of DETA, 0.7 mol/h of AEEA.

In total from 100 mol/h of EO: 31.1 mol/h of EDA, 16.1 mol/h of PIP, 3.0 mmol/h of DETA, 3.1 mol/h of AEEA and 5.4 mol/h of TEOA.

Figure 3:
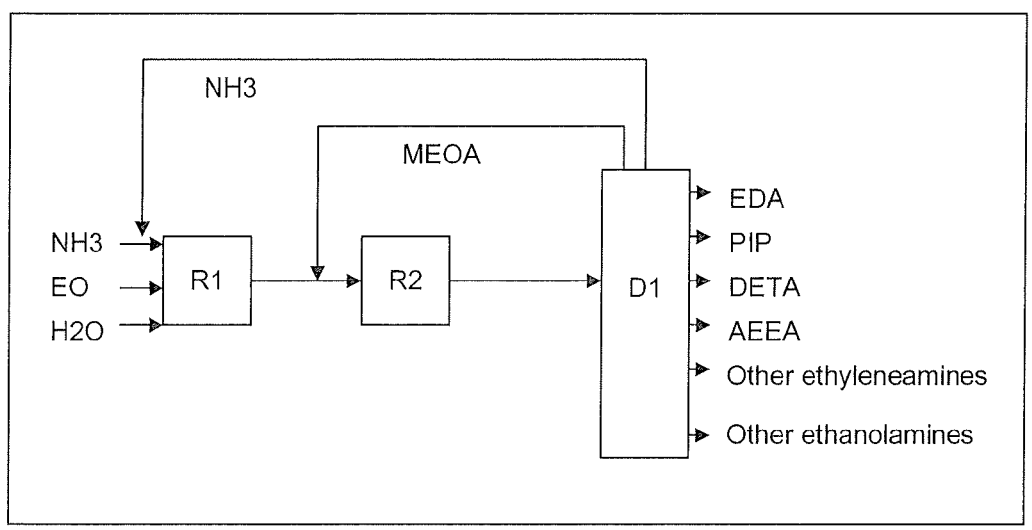
FIG. 3 shows a diagrammatic embodiment from the prior art.

The piperazine yield based on EO was 16.1 mol % and is higher compared to the prior art (cf. also FIG. 3 for a diagrammatic embodiment from the prior art):
3.6 mol % PIP yield in EP 75940 B2, therein example on pages 10-11, 220 mol/h of EO (page 10, column 18, line 38) gives 8 mol/h of piperazine (page 11, column 20, line 34), and 5 mol % PIP yield in WO 06/114417 A2, therein Example 2 on page 9, lines 30-40, 61 g/h (1.39 mol/h) of EO gives 6 g/h (0.07 mol/h) of piperazine.

The invention claimed is:

1. A process for preparing piperazine of the formula I

(I)

by reacting diethanolamine (DEOA) of the formula II

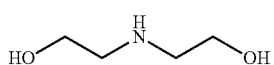
(II)

with ammonia in the presence of hydrogen and a supported, metal-containing catalyst,
wherein the catalytically active mass of the catalyst, prior to its reduction with hydrogen, comprises
a) oxygen-containing compounds of cobalt,
b) 0.2 to 5.0% by weight of oxygen-containing compounds of tin, calculated as SnO,
c) 15 to 80% by weight of oxygen-containing compounds of aluminum, calculated as Al₂O₃,
d) 1.0 to 20% by weight of oxygen-containing compounds of copper, calculated as CuO, and
e) 5.0 to 35% by weight of oxygen-containing compounds of nickel, calculated as NiO;

wherein the reaction is carried out in the liquid phase at an absolute pressure in the range from 160 to 220 bar, a temperature in the range from 180 to 220° C.,
wherein the molar ratio of ammonia to DEOA is from 5 to 25, and
wherein hydrogen is present at from 0.2 to 9.0% by weight based on the total weight of DEOA and ammonia.

2. The process according to claim 1, wherein the catalytically active mass of the catalyst, prior to its reduction with hydrogen, comprises in the range from 0.4 to 4.0% by weight of oxygen-containing compounds of tin, calculated as SnO.

3. The process according to claim 1, wherein the catalytically active mass of the catalyst, prior to its reduction with hydrogen, comprises in the range from 0.6 to 3.0% by weight of oxygen-containing compounds of tin, calculated as SnO.

4. The process according to claim 1, wherein the catalytically active mass of the catalyst, prior to its reduction with hydrogen, comprises in the range from 5.0 to 35% by weight of oxygen-containing compounds of cobalt, calculated as CoO.

5. The process according to claim 1, wherein the catalytically active mass of the catalyst, prior to its reduction with hydrogen, comprises in the range from 10 to 30% by weight of oxygen-containing compounds of cobalt, calculated as CoO.

6. The process according to claim 1, wherein the catalytically active mass of the catalyst, prior to its reduction with hydrogen, comprises from 30 to 70% by weight of oxygen-containing compounds of aluminum, calculated as Al₂O₃, 2.0 to 18% by weight of oxygen-containing compounds of copper, calculated as CuO, and 10 to 30% by weight of oxygen-containing compounds of nickel, calculated as NiO.

7. The process according to claim 1, wherein, in the catalyst, the molar ratio of nickel to copper is greater than 1.

8. The process according to claim 1, wherein no rhenium and/or ruthenium is present in the catalytically active mass of the catalyst.

9. The process according to claim 1, wherein no iron and/or zinc is present in the catalytically active mass of the catalyst.

10. The process according to claim 1, wherein no oxygen-containing compounds of silicon and/or of zirconium and/or of titanium are present in the catalytically active mass of the catalyst.

11. A process for preparing piperazine of the formula I

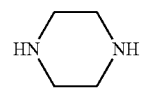
(I)

by reacting diethanolamine (DEOA) of the formula II

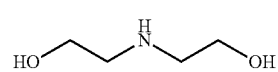
(II)

with ammonia in the presence of hydrogen and a supported, metal-containing catalyst,
wherein the catalytically active mass of the catalyst, prior to its reduction with hydrogen, comprises oxygen-containing compounds of aluminum, copper, nickel and cobalt and in the range from 0.2 to 5.0% by weight of oxygen-containing compounds of tin, calculated as SnO, wherein the reaction is carried out in the liquid phase at an absolute pressure in the range from 160 to 220 bar, a temperature in the range from 180 to 220° C.,
wherein the molar ratio of ammonia to DEOA is from 5 to 25, and wherein hydrogen is present at from 0.2 to 9.0% by weight based on the total weight of DEOA and ammonia wherein the BET surface area of the catalyst, as determined in accordance with ISO 9277:1995, is in the range from 30 to 250 m2/g.

12. The process according to claim 1, wherein the reaction is carried out at a temperature in the range from 185 to 215° C.

13. The process according to claim 1, wherein the reaction is carried out at an absolute pressure in the range from 170 to 210 bar.

14. The process according to claim 1, wherein the ammonia is used in an 8- to 23-fold molar amount, based on the DEOA used.

15. The process according to claim 1, wherein the reaction is carried out in the presence of from 0.25 to 7.0% by weight of hydrogen, based on the total amount of DEOA used and ammonia.

16. The process according to claim 1, wherein the catalyst is arranged as a fixed bed in the reactor.

17. The process according to claim 1, which is carried out continuously.

18. The process according to claim 17, wherein the reaction takes place in a tubular reactor.

19. The process according to claim 17, wherein the reaction takes place in a circulating-gas mode.

20. The process according to claim 1, wherein the DEOA is used as aqueous solution.

21. The process according to claim 1, wherein the ammonia is used as aqueous solution.

22. The process according to claim 1, wherein the reaction is carried out at a catalyst hourly space velocity in the range from 0.3 to 0.8 kg of DEOA/(lcat.·h).

23. The process according to claim 1, wherein, from the reaction product of the reaction, by distillation,
 (i) firstly separating off overhead unreacted ammonia,
 (ii) separating water off overhead,
 (iii) optionally separating present by-products with a lower boiling point than that of piperazine of the formula I

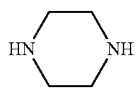

off overhead,
 (iv) separating the piperazine of the formula I off overhead, wherein optionally present by-products with a higher boiling point than that of the piperazine of the formula I and optionally present unreacted DEOA of the formula II

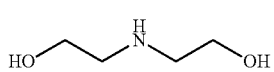

remain in the bottom.

24. The process according to claim 23, wherein, by distillation, (v) separating off overhead and returning to the reaction, by distillation, optionally present unreacted DEOA (II) and/or optionally present aminoethylethanolamine (AEEA) as by-product with the formula III

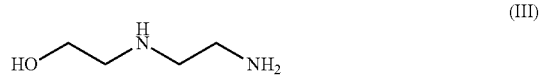

from the bottom of step iv.

25. The process according to claim 23, wherein ammonia separated off in step i and having a purity of from 90 to 99.9% by weight is returned to the reaction.

26. An integrated, multistage process for preparing piperazine, 1,2-ethylenediamine (EDA), diethylenetriamine (DETA) and N-(2-aminoethyl)ethanolamine (AEEA), comprising
 (i) reacting ethylene oxide (EO) continuously with ammonia in a first reaction stage (R1) to give a product comprising monoethanolamine (MEOA), diethanolamine (DEOA) and triethanolamine (TEOA),
 (ii) separating by distillation the MEOA, the DEOA and the TEOA in a first distillation stage (D1),
 (iii) continuously reacting the MEOA separated off in D1 with ammonia in a second reaction stage (R2) in the presence of an amination catalyst, and
 (iv) reacting the DEOA separated off in D1 with ammonia in a third reaction stage (R3) with ammonia by the process according to claim 1.

27. The process according to claim 26, wherein, in the first reaction stage, ethylene oxide (EO) is reacted with ammonia in the presence of water as catalyst.

28. The process according to claim 26, wherein water produced in distillation stage 1 (D1) and/or ammonia produced are returned to the first reaction stage (R1).

29. The process according to claim 26, wherein
 (v) separating ammonia from the reaction product of the second reaction stage (R2) by distillation in a second distillation stage (D2).

30. The process according to claim 26, wherein
 (v) separating ammonia from the reaction product of the third reaction stage (R3) by distillation in a third distillation stage (D3).

31. The process according to claim 29, further comprising
 (vi) combining the reaction product of the second reaction stage (R2) and the reaction product of the third reaction stage (R3) to form a combined product, and
 (vii) separating off by distillation piperazine, EDA, DETA and AEEA and optionally present MEOA in a fourth distillation stage (D4).

32. The process according to claim 26, further comprising
 (v) combining the reaction product of the second reaction stage (R2) and the reaction product of the third reaction stage (R3) to form a combined product,
 (vi) separating off by distillation ammonia in a third distillation stage (D3), and
 (vii) separating off by distillation piperazine, EDA, DETA and AEEA and optionally present MEOA in a fourth distillation stage (D4).

33. The process according to claim 31, further comprising
 (viii) returning the MEOA in the fourth distillation stage (D4) to the second reaction stage (R2), wherein MEOA is present in the fourth distillation stage (D4).

34. The process according to claim 32, further comprising
 (viii) returning the MEOA in the fourth distillation stage (D4) to the second reaction stage (R2), wherein MEOA is present in the fourth distillation stage (D4).

* * * * *